United States Patent
Prasse et al.

(10) Patent No.: US 9,221,846 B2
(45) Date of Patent: *Dec. 29, 2015

(54) CROSS-LINKABLE COMPOSITIONS BASED ON ORGANOSILICON COMPOUNDS

(71) Applicant: Wacker Chemie AG, Munich (DE)

(72) Inventors: Marko Prasse, Glaubitz (DE); Michael A. Brook, Ancaster (CA); Uwe Scheim, Coswig (DE); Yang Chen, Ancaster (CA)

(73) Assignee: WACKER CHEMIE AG, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/376,765

(22) PCT Filed: Feb. 26, 2013

(86) PCT No.: PCT/EP2013/053790
§ 371 (c)(1),
(2) Date: Aug. 5, 2014

(87) PCT Pub. No.: WO2013/127774
PCT Pub. Date: Sep. 6, 2013

(65) Prior Publication Data
US 2015/0011705 A1    Jan. 8, 2015

(30) Foreign Application Priority Data
Mar. 1, 2012 (DE) .................. 10 2012 203 273

(51) Int. Cl.
| | | |
|---|---|---|
| *C08L 83/04* | (2006.01) |
| *C07F 7/08* | (2006.01) |
| *C07F 7/18* | (2006.01) |
| *C08G 77/14* | (2006.01) |
| *C08G 77/26* | (2006.01) |
| *C08K 3/36* | (2006.01) |

(52) U.S. Cl.
CPC ............. *C07F 7/0818* (2013.01); *C07F 7/1836* (2013.01); *C08G 77/14* (2013.01); *C08G 77/26* (2013.01); *C08K 3/36* (2013.01); *C08L 83/04* (2013.01)

(58) Field of Classification Search
None
See application file for complete search history.

(56) References Cited

U.S. PATENT DOCUMENTS

| | | | | |
|---|---|---|---|---|
| 4,844,980 A | * | 7/1989 | Gruning et al. | 428/405 |
| 5,314,533 A | * | 5/1994 | Goebel et al. | 106/287.13 |
| 6,303,678 B1 | | 10/2001 | Ziche et al. | |
| 7,582,717 B2 | | 9/2009 | Schoeley et al. | |
| 7,998,588 B2 | | 8/2011 | Sakamoto et al. | |
| 2008/0210906 A1 | * | 9/2008 | Kawazu et al. | 252/301.35 |
| 2010/0105817 A1 | * | 4/2010 | Arkles et al. | 524/265 |

FOREIGN PATENT DOCUMENTS

| EP | 1036820 B1 | 9/2000 |
|---|---|---|
| EP | 1803777 B1 | 7/2007 |

OTHER PUBLICATIONS

"Direct Hydrothermal Synthesis of Hierarchically Porous Siliceous Zeolite by Using Alkoxysilylated Nonionic Surfactant" authored by Mukti et al. and published in Langmuir (2010) 26(4) 2731-2735.*
The abstract for JP 4-180916 (Jun. 1992).*

* cited by examiner

*Primary Examiner* — Marc Zimmer
(74) *Attorney, Agent, or Firm* — Brooks Kushman P.C.

(57) ABSTRACT

Moisture curable RTV-1 silicone elastomers with hydrophilic surfaces are produced from crosslinkable compositions containing a polyoxyethylene ether glycol terminated with both a $C_{6-22}$ hydrocarbon group and an alkoxysilyl group.

12 Claims, No Drawings

CROSS-LINKABLE COMPOSITIONS BASED ON ORGANOSILICON COMPOUNDS

CROSS-REFERENCE TO RELATED APPLICATIONS

This application is the U.S. National Phase of PCT Appln. No. PCT/EP2013/053790 filed Feb. 26, 2013, which claims priority to German application DE 10 2012 203 273.8 filed Mar. 1, 2012, the disclosures of which are incorporated in their entirety by reference herein.

BACKGROUND OF THE INVENTION

1. Field of the Invention

The invention relates to compositions based on organosilicon compounds, storable with the exclusion of water, and crosslinkable upon ingress of water at room temperature to form elastomers, where the elastomers have hydrophilic surfaces, to methods for their production and to the use thereof.

2. Description of the Related Art

Crosslinkable compositions based on organosilicon compounds with different types of feed materials are widely known, such as e.g. single-component sealant compositions, storable with the exclusion of water and vulcanizable upon ingress of water at room temperature to provide elastomers (RTV-1). These products are used in large amounts e.g. in the construction industry. The basis of these mixtures are polymers which are terminated by silyl groups which carry reactive substituents such as OH groups, or hydrolyzable groups such as alkoxy groups. Usually, such compositions and/or their vulcanizates are hydrophobic; water drops do not readily run off, but dry on the surface. Consequently, materials which are dissolved or dispersed in water, are deposited on the surface after drying.

It is thus desirable to obtain single-component sealant compositions that are vulcanizable upon ingress of water at room temperature to elastomers which have a hydrophilic surface and consequently dry more quickly and have fewer deposits.

EP 1 036 820 A describes RTV-1 alkoxy compositions with surfactants. The surfactants may be polyethylene glycols which have C6-C20-alkyl end groups on both ends, or may be polydimethylsiloxanes with polyether groups.

EP 1 803 777 A describes RTV-1 compositions with polyethers, where the polyethers can be silylated. The polyethers are OH-terminated.

U.S. Pat. No. 7,998,588 A describes RTV-1 compositions which comprise polyethers silylated at one or both ends. The polyether silylated at one end can contain an alkyl radical having up to 6 carbon atoms at the other end.

SUMMARY OF THE INVENTION

It has now been surprisingly and unexpectedly discovered that RTV-01 moisture-curable organopolysiloxane compositions which, when cured, offer hydrophilic surfaces, can be prepared by incorporating into the curable composition, a polyoxyethylene glycol terminated on one end by a $C_{8-22}$ hydrocarbon radical and on the other end by an alkoxysilyl group linked to the polyether by a linking group.

DETAILED DESCRIPTION OF THE PREFERRED EMBODIMENTS

The invention thus provides single-component compositions, storable with the exclusion of water and crosslinkable upon ingress of water at room temperature to form elastomers, based on organosilicon compounds comprising compounds of the formula $$(R^1O)_a R_{3-a} Si\text{-}A\text{-}O(CH_2CH_2\text{—}O)_x\text{—}R^2 \qquad (I),$$

where

R can be identical or different and is a monovalent, optionally substituted hydrocarbon radical, $R^1$ can be identical or different and is hydrogen or a monovalent, optionally substituted hydrocarbon radical, A is a divalent, optionally substituted hydrocarbon radical bonded via carbon onto Si and O, which optionally contains hydroxyl, ester (—O—C(=O)—), amide (—N—C(=O)—), urethane (—O—C(=O)—NH—), urea (—N—C(=O)—NH—), thioester (—S—C(=O)—), thioether (—S—), ether (—O—), imine (—NH—) and/or carbonyl groups (—C(=O)—), $R^2$ is a monovalent, linear or branched hydrocarbon radical having 8 to 22 carbon atoms, bonded via carbon onto O, where a carbon atom can be replaced by a silicon atom, a is 1, 2 or 3, preferably 2 or 3, in particular 3, and x is an integer from 1 to 20, preferably an integer from 2 to 15, more preferably an integer from 2 to 10.

Examples of radicals R are alkyl radicals such as the methyl, ethyl, n-propyl, isopropyl, 1-n-butyl, 2-n-butyl, isobutyl, tert-butyl, n-pentyl, isopentyl, neopentyl, and tert-pentyl radicals; hexyl radicals such as the n-hexyl radical; heptyl radicals such as the n-heptyl radical; octyl radicals such as the n-octyl radical, isooctyl radicals and the 2,2,4-trimethylpentyl radical; nonyl radicals such as the n-nonyl radical; decyl radicals such as the n-decyl radical; dodecyl radicals such as the n-dodecyl radical; octadecyl radicals such as the n-octadecyl radical; cycloalkyl radicals such as the cyclopentyl, cyclohexyl, cycloheptyl, and methylcyclohexyl radicals; alkenyl radicals such as the vinyl, 1-propenyl and 2-propenyl radicals; aryl radicals such as the phenyl, naphthyl, anthryl and phenanthryl radicals; alkaryl radicals such as o-, m-, p-tolyl radicals, xylyl radicals and ethylphenyl radicals; and aralkyl radicals such as the benzyl radical, and the α- and β-phenylethyl radicals.

Preferably, radical R is a hydrocarbon radical having 1 to 12 carbon atoms, more preferably a methyl, ethyl, vinyl or phenyl radical, and in particular the methyl radical.

Examples of optionally substituted hydrocarbon radicals $R^1$ are the examples given for radical R.

The radicals $R^1$ are preferably hydrogen or hydrocarbon radicals having 1 to 18 carbon atoms, more preferably hydrogen or hydrocarbon radicals having 1 to 10 carbon atoms, in particular, hydrogen, methyl, or ethyl radicals.

Examples of radicals $R^2$ are the examples having 8 to 22 carbon atoms given for radical R, as well as alkyl radicals such as the lauryl, isotridecyl, palmitoyl and stearyl radicals; cycloalkyl radicals such as the cyclohexylbutyl radical; alkenyl radicals such as the undecenyl, hexadecenyl and oleyl radicals; and also radicals in which a carbon atom is replaced by a silicon atom, such as the 3-(triethylsilyl)propyl or the 3-(tri-n-hexylsilyl)propyl radicals.

The radicals $R^2$ are preferably hydrocarbon radicals having 8 to 20 carbon atoms, in particular octyl radicals such as the n-octyl radical, isooctyl radicals and the 2,2,4-trimethylpentyl radical; nonyl radicals such as the n-nonyl radical; decyl radicals such as the n-decyl radical; dodecyl radicals such as the n-dodecyl radical; tridecyl radicals such as the isotridecyl radical; hexadecyl radicals such as the n-hexadecyl radical; octadecyl radicals such as the n-octadecyl radical; cycloalkyl radicals such as the 4-cyclohexylbutyl radical, and alkenyl radicals such as the undecenyl, hexadecenyl and oleyl radical.

Preferred radicals for A are —CH$_2$CH$_2$CH$_2$OCH$_2$CH(OH)CH$_2$OC(=O)CH$_2$—, —CH$_2$CH$_2$CH$_2$OCH$_2$CH(CH$_2$(OH))OC(=O)CH$_2$—, —CH$_2$CH$_2$CH$_2$CH$_2$CH(OH)CH$_2$OC(=O)CH$_2$—, —CH$_2$CH$_2$CH$_2$CH$_2$CH(CH$_2$OH)OC(=O)CH$_2$—,

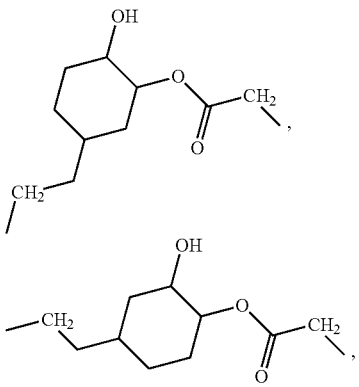

—C(=O)—NH—CH$_2$—CH$_2$—CH$_2$—, —C(=O)—NH—CH$_2$—, —CH$_2$CH$_2$CH$_2$NHC(=O)CH$_2$—, —CH$_2$CH$_2$CH$_2$NHCH$_2$CH$_2$NHC(=O)CH$_2$—, —CH$_2$CH$_2$CH$_2$S—C(=O)CH$_2$—, —CH$_2$CH$_2$CH$_2$NHC(=O)NH—CH(CH$_3$)CH$_2$—, —C(=O)CH(CH$_3$)CH$_2$NHCH$_2$CH$_2$CH$_2$—, —C(=O)CH$_2$—NHCH$_2$CH$_2$CH$_2$—, —C(=O)C(CH$_3$)$_2$NHCH$_2$CH$_2$CH$_2$—, —C(=O)CH(CH$_3$)—NHCH$_2$CH$_2$CH$_2$—, —C(=O)CH(CH$_3$)CH$_2$NHCH$_2$CH$_2$NHCH$_2$CH$_2$CH$_2$—, —C(=O)C(CH$_3$)$_2$NHCH$_2$H$_2$NHCH$_2$CH$_2$CH$_2$—, —CH$_2$CH$_2$—, —CH$_2$—, —C(=O)CH$_2$CH$_2$NHCH$_2$CH$_2$NHCH$_2$CH$_2$CH$_2$—, —C(=O)CH(CH$_3$)NHCH$_2$CH$_2$NHCH$_2$CH$_2$CH$_2$—, —CH$_2$CH$_2$CH$_2$NHCH$_2$CH(OH)CH$_2$—, —CH$_2$CH$_2$CH$_2$NHCH$_2$CH$_2$NHCH$_2$CH(OH)CH$_2$—, —CH$_2$CH$_2$CH$_2$SCH$_2$CH(OH)CH$_2$—, —CH$_2$CH$_2$CH$_2$NHCH(CH$_2$OH)CH$_2$—, —CH$_2$CH$_2$CH$_2$NHCH$_2$CH$_2$NHCH(CH$_2$OH)CH$_2$— and —CH$_2$CH$_2$CH$_2$SCH(CH$_2$OH)CH$_2$—.

Particularly preferably, radical A is —CH$_2$CH$_2$CH$_2$OCH$_2$CH(OH)CH$_2$OC(=O)CH$_2$—, —CH$_2$CH$_2$CH$_2$OCH$_2$CH(CH$_2$(OH))OC(=O)CH$_2$—, —C(=O)—NH—CH$_2$—CH$_2$—CH$_2$—, —C(=O)—NH—CH$_2$—, —CH$_2$CH$_2$CH$_2$NHC(=O)CH$_2$—, —CH$_2$CH$_2$CH$_2$NHCH$_2$CH$_2$NHC(=O)CH$_2$—, —CH$_2$CH$_2$CH$_2$NHC(=O)NH—CH(CH$_3$)CH$_2$—, —C(=O)CH(CH$_3$)CH$_2$NHCH$_2$CH$_2$CH$_2$—, —C(=O)CH$_2$CH$_2$—NHCH$_2$CH$_2$CH$_2$—, —C(=O)C(CH$_3$)$_2$NHCH$_2$CH$_2$CH$_2$—, —C(=O)CH(CH$_3$)—NHCH$_2$CH$_2$CH$_2$—, —C(=O)CH(CH$_3$)CH$_2$NHCH$_2$CH$_2$NHCH$_2$CH$_2$CH2—, —C(=O)C(CH$_3$)$_2$NHCH$_2$CH$_2$NHCH$_2$CH$_2$CH$_2$—, —CH$_2$CH$_2$CH$_2$—, —CH$_2$—, —C(=O)CH$_2$H$_2$NHH$_2$CH$_2$NHCH$_2$CH$_2$CH$_2$—, —C(=O)CH(CH$_3$)NHCH$_2$CH$_2$NHCH$_2$CH$_2$CH$_2$—, —CH$_2$CH$_2$CH$_2$NHCH$_2$CH(OH)CH$_2$—, —CH$_2$CH$_2$CH$_2$NHCH$_2$CH$_2$NHCH$_2$CH(OH)CH$_2$—, —CH$_2$CH$_2$CH$_2$NHCH(CH$_2$OH)CH$_2$— or —CH$_2$CH$_2$CH$_2$NHCH$_2$CH$_2$NHCH(CH$_2$OH)CH$_2$.

Examples of compounds of the formula (I) are (MeO)$_3$Si—CH$_2$CH$_2$CH$_2$OCH$_2$CH(OH)CH$_2$OC(=O)CH$_2$—O(CH$_2$CH$_2$O)$_{2-6}$—C$_8$H$_{17}$, (EtO)$_2$MeSi—CH$_2$CH$_2$CH$_2$OCH$_2$CH(OH)CH$_2$OC(=O)CH$_2$—O(CH$_2$CH$_2$O)$_{2-6}$—C$_8$H$_{17}$, (MeO)$_3$Si—CH$_2$CH$_2$CH$_2$OCH$_2$CH(OH)CH$_2$OC(=O)CH$_2$—O(CH$_2$CH$_2$O)$_{5-8}$—(CH$_2$)$_{11-13}$CH$_3$, (EtO)$_3$Si—CH$_2$CH$_2$CH$_2$OCH$_2$CH(OH)CH$_2$OC(=O)CH$_2$—O(CH$_2$CH$_2$O)$_{2-6}$—(CH$_2$)$_{11-13}$CH$_3$, (MeO)$_2$MeSi—CH$_2$CH$_2$CH$_2$OCH$_2$CH(OH)CH$_2$OC(=O)CH$_2$—O(CH$_2$CH$_2$O)$_{8-12}$-iso-C$_{13}$H$_{27}$, (EtO)$_3$Si—CH$_2$CH$_2$CH$_2$OCH$_2$CH(OH)CH$_2$OC(=O)CH$_2$—O(CH$_2$CH$_2$O)$_{2-6}$-iso-C$_{13}$H$_{27}$, (MeO)$_2$HOSi—CH$_2$CH$_2$CH$_2$OCH$_2$CH(OH)CH$_2$OC(=O)CH$_2$—O(CH$_2$CH$_2$O)$_{2-6}$—(CH$_2$)$_8$CH=CH(CH$_2$)$_{5-7}$CH$_3$, (HO)$_3$Si—CH$_2$CH$_2$CH$_2$OCH$_2$CH(OH)CH$_2$OC(=O)CH$_2$—O(CH$_2$CH$_2$O)$_{2-6}$—(CH$_2$)$_8$CH=CH(CH$_2$)$_{5-7}$CH$_3$, (MeO)$_2$MeSi—CH$_2$CH$_2$CH$_2$OCH$_2$CH(CH$_2$OH)OC(=O)CH$_2$—O(CH$_2$CH$_2$O)$_{2-6}$—C$_8$H$_{17}$, (EtO)$_3$Si—CH$_2$CH$_2$CH$_2$OCH$_2$CH(CH$_2$OH)OC(=O)CH$_2$—O(CH$_2$CH$_2$O)$_{2-6}$—C$_8$H$_{17}$, (MeO)$_3$Si—CH$_2$CH$_2$CH$_2$OCH$_2$CH(CH$_2$OH)OC(=O)CH$_2$—O(CH$_2$CH$_2$O)$_{5-8}$—(CH$_2$)$_{11-13}$CH$_3$, (EtO)$_2$HOSi—CH$_2$CH$_2$CH$_2$OCH$_2$CH(CH$_2$OH)OC(=O)CH$_2$—O(CH$_2$CH$_2$O)$_{2-6}$—(CH$_2$)$_{11-13}$CH$_3$, (MeO)$_3$Si—CH$_2$CH$_2$CH$_2$OCH$_2$CH(CH$_2$OH)OC(=O)CH$_2$—O(CH$_2$CH$_2$O)$_{8-12}$-iso-C$_{13}$H$_{27}$, (EtO)$_3$Si—CH$_2$CH$_2$CH$_2$OCH$_2$CH(CH$_2$(OH))OC(=O)CH$_2$—O(CH$_2$CH$_2$O)$_{2-6}$-iso-C$_{13}$H$_{27}$, (MeO)(HO)$_2$Si—CH$_2$H$_2$CH$_2$OCH$_2$CH(CH$_2$OH)OC(=O)CH$_2$—O(CH$_2$CH$_2$O)$_{2-6}$—(CH$_2$)$_8$CH=CH(CH$_2$)$_{5-7}$CH$_3$, (EtO)$_3$Si—CH$_2$CH$_2$H$_2$CH$_2$H(CH$_2$OH)OC(=O)CH$_2$—O(CH$_2$CH$_2$)$_{2-6}$—(CH$_2$)$_8$CH=CH(CH$_2$)$_{5-7}$CH$_3$, (MeO)$_3$Si—CH$_2$CH$_2$CH$_2$CH$_2$CH(OH)CH$_2$OC(=O)CH$_2$—O(CH$_2$CH$_2$O)$_{2-6}$—C$_8$H$_{17}$, (EtO)$_2$MeSi—CH$_2$CH$_2$CH$_2$CH$_2$CH(OH)CH$_2$OC(=O)CH$_2$—O(CH$_2$CH$_2$O)$_{2-6}$—C$_8$H$_{17}$, (MeO)$_2$MeSi—CH$_2$CH$_2$CH$_2$CH$_2$CH(CH$_2$OH)OC(=O)CH$_2$—O(CH$_2$CH$_2$O)$_{2-6}$—C$_8$H$_{17}$, (EtO)$_3$Si—CH$_2$CH$_2$CH$_2$CH$_2$CH(CH$_2$OH)OC(=O)CH$_2$—O(CH$_2$CH$_2$O)$_{2-6}$—C$_8$H$_{17}$,

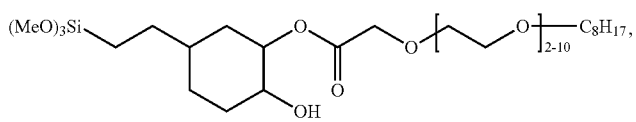

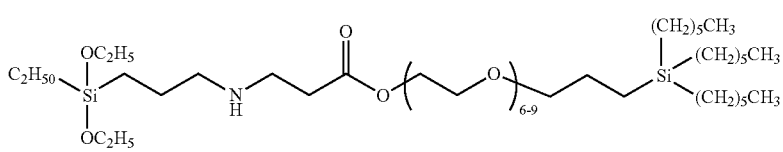

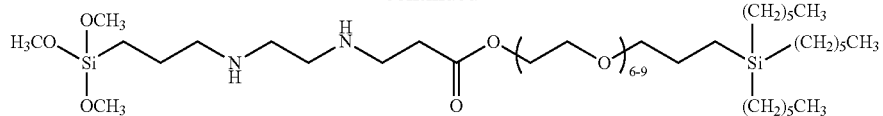

$(MeO)_3Si—CH_2CH_2CH_2NC(=O)—O(CH_2CH_2O)_{2-6}—C_8H_{17}$, $(EtO)_3SiCH_2NC(=O)—O(CH_2CH_2O)_{2-6}—C_8H_{17}$, $(EtO)_2MeSiCH_2NC(=O)—O(CH_2CH_2O)_{2-6}—C_8H_{17}$, $(MeO)_2MeSi—CH_2CH_2CH_2NHC(=O)CH_2—O(CH_2CH_2O)_{2-6}—C_8H_{17}$, $(MeO)_3Si—CH_2CH_2CH_2 NHCH_2CH_2NHC(=O)CH_2—O(CH_2CH_2O)_{5-8}—(CH_2)_{11-13} CH_3$, $(MeO)_3Si—CH_2CH_2CH_2NHC(=O)NHCH(CH_3)CH_2—O(CH_2CH_2O)_{2-6}—(CH_2)_{11-13}CH_3$, $(EtO)_2MeSi—CH_2NHC(=O)NHCH(CH_3)CH_2—O(CH_2CH_2O)_{2-6}—(CH_2)_{11-13}CH_3$, $(MeO)_2MeSi—CH_2CH_2CH_2NHCH_2CH_2C(=O)—O(CH_2CH_2O)_{8-12}\text{-iso-}C_{13}H_{27}$, $(MeO)_2MeSi—CH_2CH_2CH_2NHCH(CH_3)C(=O)—O(CH_2CH_2O)_{8-12}\text{-iso-}C_{13}H_{27}$, $(MeO)_2MeSi—CH_2CH_2CH_2NHCH_2CH(CH_3)C(=O)—O(CH_2CH_2O)_{8-12}\text{-iso-}C_{13}H_{27}$, $(MeO)_2MeSi—CH_2CH_2CH_2NHC(CH_3)_2C(=O)—O(CH_2CH_2O)_{8-12}\text{-iso-}C_{13}H_{27}$, $(MeO)_3Si—CH_2CH_2CH_2NHCH_2CH_2NHCH_2C(=O)—O(CH_2CH_2O)_{8-12}\text{-iso-}C_{13}H_{27}$, $(MeO)_3Si—CH_2CH_2CH_2NHCH_2CH_2NHCH(CH_3)C(=O)—O(CH_2CH_2O)_{8-12}\text{-iso-}C_{13}H_{27}$, $(MeO)_3Si—CH_2CH_2CH_2NHCH_2 H_2NHCH_2CH(CH_3)C(=O)—O(CH_2CH_2O)_{5-7}—C_8H_{17}$, $(MeO)_3Si—CH_2CH_2CH_2NHCH_2CH_2NHC(CH_3)_2C(=O)—O(CH_2CH_2O)_{5-7}—C_8H_{17}$, $(MeO)_3Si—CH_2CH_2CH_2—O(CH_2CH_2O)_{5-7}—C_8H_{17}$, $(MeO)_3Si—CH_2—O(CH_2CH_2O)_{5-7}—C_8H_{17}$, $(EtO)_3Si—CH_2H_2CH_2—O(CH_2CH_2O)_{4-6}—C_8H_{17}$, $(EtO)_3Si—CH_2—O(CH_2CH_2O)_{3-5}—C_{12}H_{25}$, $(HO)_3Si—CH_2CH_2CH_2—O(CH_2CH_2O)_{5-7}—C_8H_{17}$, $(HO)_3Si—CH_2—O(CH_2CH_2O)_{5-7}—C_8H_{17}$, $(EtO)_3Si—CH_2CH_2CH_2NHCH_2CH(OH)CH_2—O(CH_2CH_2O)_{2-6}\text{-iso-}C_{13}H_{27}$, $(EtO)_3Si—CH_2CH_2CH_2NHCH(CH_2OH)CH_2—O(CH_2CH_2O)_{2-6}\text{-iso-}C_{13}H_{27}$, $(MeO)_2HOSi—CH_2CH_2CH_2NHCH_2CH_2NHCH_2CH(OH)CH_2—O(CH_2CH_2O)_{2-6}—(CH_2)_8CH=CH(CH_2)_{5-7} CH_3$ and $(HO)_3Si—CH_2CH_2CH_2NHCH_2CH_2NHCH(CH_2OH)CH_2—O(CH_2CH_2O)_{2-6}—(CH_2)_8CH=CH(CH_2)_{5-7}CH_3$, $CH_2CH_2CH_2OCH_2CH(OH)CH_2OC(=O)CH_2—O(CH_2CH_2O)_{2-15}\text{-iso-}C_{13}H_{27}$, $(MeO)_3Si—CH_2CH_2CH_2OCH_2CH(OH)CH_2OC(=O)CH_2—O(CH_2CH_2O)_{2-15}—(CH_2)_8CH=CH(CH_2)_{5-7}CH_3$, $(EtO)_3Si—CH_2CH_2CH_2OCH_2CH(OH)CH_2OC(=O)CH_2—O(CH_2CH_2O)_{2-15}—(CH_2)_8CH=CH(CH_2)_{5-7}CH_3$, $(MeO)_3Si—CH_2H_2CH_2OCH_2CH(CH_2OH)OC(=O)CH_2—O(CH_2CH_2O)_{2-15}—C_8H_{17}$, $(EtO)_3Si—CH_2H_2CH_2OCH_2CH(CH_2OH)OC(=O)CH_2—O(CH_2CH_2O)_{2-15}—C_8H_{17}$, $(MeO)_3Si—CH_2CH_2CH_2OCH_2CH(CH_2OH)OC(=O)CH_2—O(CH_2CH_2O)_{2-15}—(CH_2)_{11-13}CH_3$, $(EtO)_3Si—CH_2CH_2CH_2OCH_2CH(CH_2OH)OC(=O)CH_2—O(CH_2CH_2O)_{2-15}—(CH_2)_{11-13}CH_3$, $(MeO)_3Si—CH_2H_2CH_2OCH_2CH(CH_2OH)OC(=O)CH_2—O(CH_2CH_2O)_{2-15}\text{-iso-}C_{13}H_{27}$, $(EtO)_3Si—CH_2CH_2CH_2OCH_2CH(CH_2(OH))OC(=O)CH_2—O(CH_2CH_2O)_{2-15}\text{-iso-}C_{13}H_{27}$, $(MeO)_3Si—CH_2CH_2CH_2OCH_2CH(CH_2OH)OC(=O)CH_2—O(CH_2CH_2O)_{2-15}—(CH_2)_8CH=CH(CH_2)_{5-7}CH_3$, $(EtO)_3Si—CH_2CH_2CH_2OCH_2CH(CH_2OH)OC(=O)CH_2—O(CH_2CH_2O)_{2-15}—(CH_2)_8CH=CH(CH_2)_{5-7}CH_3$, $(MeO)_3SiCH_2CH_2CH_2NC(=O)—O(CH_2CH_2O)_{2-15}—C_8H_{17}$, $(EtO)_2MeSiCH_2NC(=O)—O(CH_2CH_2O)_{2-15}—C_8H_{17}$, $(MeO)_3SiCH_2CH_2CH_2NC(=O)—O(CH_2CH_2O)_{2-15}—C_{12}H_{25}$, $(EtO)_2MeSiCH_2NC(=O)—O(CH_2CH_2O)_{2-15}—C_{12}H_{25}$, $(MeO)_3SiCH_2CH_2CH_2NC(=O)—O(CH_2CH_2O)_{2-15}\text{-iso-}C_{13}H_{27}$, $(EtO)_2MeSiCH_2NC(=O)—O(CH_2CH_2O)_{2-15}\text{-iso-}C_{13}H_{27}$, $(MeO)_3Si—CH_2CH_2CH_2NHC(=O)NHCH(CH_3)CH_2—O(CH_2CH_2O)_{2-15}—(CH_2)_7CH_3$, $(EtO)_2MeSi—CH_2NHC(=O)NHCH(CH_3)CH_2—O(CH_2CH_2O)_{2-15}—(CH_2)_7CH_3$, $(MeO)_3Si—CH_2CH_2CH_2NHC(=O)NHCH(CH_3)CH_2—O(CH_2CH_2O)_{2-15}—(CH_2)_{11-13}CH_3$, $(EtO)_2MeSi—CH_2NHC(=O)NHCH(CH_3)CH_2—O(CH_2CH_2O)_{2-15}—(CH_2)_{11-13}CH_3$,

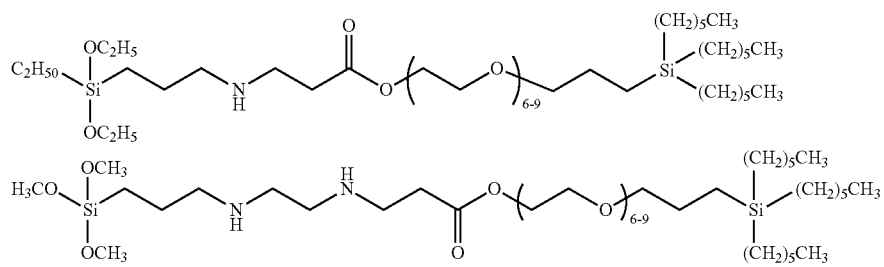

where Me is the methyl radical and Et is the ethyl radical.

Preferably, the compounds of the formula (I) used according to the invention are $(MeO)_3Si—CH_2CH_2CH_2OCH_2CH(OH)CH_2OC(=O)CH_2—O(CH_2CH_2O)_{2-15}—C_8H_{17}$, $(EtO)_3 Si—CH_2CH_2CH_2OCH_2CH(OH)CH_2OC(=O)CH_2—O(CH_2CH_2O)_{2-15}—C_8H_{17}$, $(MeO)_3Si—CH_2 CH_2 CH_2OCH_2CH(OH)CH_2OC(=O)CH_2—O(CH_2CH_2O)_{2-15}—(CH_2)_{11-13}CH_3$, $(EtO)_3Si—CH_2CH_2CH_2OCH_2CH(OH)CH_2OC(=O)CH_2—O(CH_2CH_2O)_{2-15}—(CH_2)_{11-13}CH_3$, $(MeO)_3Si—CH_2CH_2CH_2OCH_2CH(OH)CH_2OC(=O)CH_2—O(CH_2CH_2O)_{2-15}\text{-iso-}C_{13}H_{27}$, $(EtO)_3Si—CH_2CH_2CH_2OCH_2CH(OH)CH_2OC(=O)CH_2—O(CH_2CH_2O)_{2-15}—C_8H_{17}$, $(MeO)_3Si—H_2CH_2CH_2NHCH_2CH_2C(=O)—O(CH_2CH_2O)_{2-15}—C_8H_{17}$, $(MeO)_3Si—H_2CH_2CH_2 NHCH_2CH_2C(=O)—O(CH_2CH_2O)_{2-15}—C_{12}H_{25}$, $(MeO)_3Si—H_2CH_2CH_2NHCH_2CH_2C(=O)—O(CH_2CH_2O)_{2-15}\text{-iso-}C_{13}H_{27}$, $(MeO)_3Si—H_2CH_2CH_2NHCH(CH_3)—O(=O)—O(CH_2CH_2O)_{2-15}—C_8H_{17}$, $(MeO)_3Si—H_2CH_2CH_2NHCH(CH_3)—O(=O)—O(CH_2CH_2O)_{2-15}—C_{12}H_{25}$, $(MeO)_3Si—CH_2CH_2CH_2NHCH(CH_3)—O(=O)—O(CH_2CH_2O)_{2-15}\text{-iso-}C_{13}H_{27}$, $(MeO)_3Si—H_2CH_2CH_2NHCH_2CH_2NHCH_2 CH_2 C(=O)—O(CH_2CH_2O)_{2-15}—C_8H_{17}$, $(MeO)_3Si—H_2CH_2CH_2NHCH_2CH_2NHCH_2CH_2C(=O)—O $(CH_2CH_2O)_{2-15}$—$C_{12}H_{25}$, $(MeO)_3Si$—$H_2H_2CH_2NHCH_2$ $CH_2NHCH_2CH_2C(=O)$—$O(CH_2CH_2O)_{2-15}$-iso-$C_{13}H_{27}$, $(MeO)_3Si$—$CH_2CH_2CH_2$—$O(CH_2CH_2O)_{2-15}$—$C_8H_{17}$, $(MeO)_3Si$—$CH_2CH_2CH_2$—$O(CH_2CH_2O)_{2-15}$—$C_{12}H_{25}$, $(MeO)_3Si$—$CH_2CH_2CH_2$—$O(CH_2CH_2O)_{2-15}$-iso-$C_{13}H_{27}$, $(EtO)_2MeSi$—$CH_2$—$O(CH_2CH_2O)_{2-15}$—$C_8H_{17}$, $(EtO)_2MeSi$—$CH_2$—$O(CH_2CH_2O)_{2-15}$—$C_{12}H_{25}$, $(EtO)_2MeSi$—$CH_2$—$O(CH_2CH_2O)_{2-15}$-iso-$C_{13}H_{27}$, $(MeO)_3Si$—$H_2CH_2CH_2NHCH_2CH(OH)CH_2$—$O(CH_2CH_2O)_{2-15}$—$C_8H_{17}$, $(MeO)_3Si$—$CH_2CH_2CH_2NHCH_2CH(CH_2OH)CH_2$—$O(CH_2CH_2O)_{2-15}$—$C_8H_{17}$, $(MeO)_3Si$—$CH_2CH_2CH_2NHCH_2CH(OH)CH_2$—$O(CH_2CH_2O)_{2-15}$—$C_{12}H_{25}$, $(MeO)_3Si$—$CH_2CH_2CH_2NHCH_2CH(CH_2OH)CH_2$—$O(CH_2CH_2O)_{2-15}$—$C_{12}H_{25}$, $(MeO)_3Si$—$CH_2CH_2CH_2NHCH_2CH(OH)CH_2$—$O(CH_2CH_2O)_{2-15}$-iso-$C_{13}H_{27}$ and $(MeO)_3Si$—$CH_2CH_2CH_2NHCH(CH_2OH)CH_2$—$O(CH_2CH_2O)_{2-15}$-iso-$C_{13}H_{27}$, particularly preferably $(MeO)_3Si$—$CH_2CH_2CH_2OCH_2CH(OH)CH_2OC(=O)CH_2$—$O(CH_2CH_2O)_{2-10}$—$C_8H_{17}$, $(EtO)_3Si$—$CH_2CH_2CH_2OCH_2CH(OH)CH_2OC(=O)CH_2$—$O(CH_2CH_2O)_{2-10}$—$C_8H_{17}$, $(MeO)_3Si$—$CH_2CH_2CH_2OCH_2CH(OH)CH_2OC(=O)CH_2$—$O(CH_2CH_2O)_{2-10}$—$(CH_2)_{11-13}CH_3$, $(EtO)_3Si$—$CH_2CH_2CH_2OCH_2CH(OH)CH_2OC(=O)CH_2$—$O(CH_2CH_2O)_{2-10}$—$(CH_2)_{11-13}CH_3$, $(MeO)_3Si$—$CH_2CH_2CH_2OCH_2CH(CH_2OH)OC(=O)CH_2$—$O(CH_2CH_2O)_{2-10}$—$C_8H_{17}$, $(EtO)_3Si$—$CH_2CH_2CH_2OCH_2CH(CH_2OH)OC(=O)CH_2$—$O(CH_2CH_2O)_{2-10}$—$C_8H_{17}$, $(MeO)_3Si$—$CH_2CH_2CH_2OCH_2CH(CH_2OH)OC(=O)CH_2$—$O(CH_2CH_2O)_{2-10}$—$(CH_2)_{11-13}CH_3$, $(EtO)_3Si$—$CH_2CH_2CH_2OCH_2CH(CH_2OH)OC(=O)CH_2$—$O(CH_2CH_2O)_{2-10}$—$(CH_2)_{11-13}CH_3$, $(MeO)_3SiCH_2CH_2CH_2NC(=O)$—$O(CH_2CH_2O)_{2-10}$—$C_8H_{17}$, $(EtO)_2MeSiCH_2NC(=O)$—$O(CH_2CH_2O)_{2-10}$—$C_8H_{17}$, $(MeO)_3SiCH_2CH_2CH_2NC(=O)$—$O(CH_2CH_2O)_{2-10}$—$C_{12}H_{25}$, $(EtO)_2MeSiCH_2NC(=O)$—$O(CH_2CH_2O)_{2-10}$—$C_{12}H_{25}$, $(MeO)_3Si$—$CH_2CH_2CH_2NHCH_2CH_2C(=O)$—$O(CH_2CH_2O)_{2-10}$—$C_8H_{17}$, $(MeO)_3Si$—$CH_2CH_2CH_2NHCH_2CH_2C(=O)$—$O(CH_2CH_2O)_{2-10}$—$C_{12}H_{25}$, $(MeO)_3Si$—$CH_2CH_2CH_2NHCH_2CH(CH_3)$—$O(=O)$—$O(CH_2CH_2O)_{2-10}$—$C_8H_{17}$, $(MeO)_3Si$—$CH_2CH_2CH_2NHCH_2CH(CH_3)$—$O(=O)$—$O(CH_2CH_2O)_{2-10}$—$C_{12}H_{25}$, $(MeO)_3Si$—$CH_2CH_2CH_2NHCH_2CH_2NHCH_2CH_2C(=O)$—$O(CH_2CH_2O)_{2-10}$—$C_8H_{17}$, $(MeO)_3Si$—$CH_2CH_2CH_2NHCH_2CH_2NHCH_2CH_2C(=O)$—$O(CH_2CH_2O)_{2-10}$—$C_{12}H_{25}$, $(MeO)_3Si$—$CH_2CH_2CH_2$—$O(CH_2CH_2O)_{2-10}$—$C_8H_{17}$, $(MeO)_3Si$—$CH_2CH_2CH_2$—$O(CH_2CH_2O)_{2-10}$—$C_{12}H_{25}$, $(EtO)_2MeSi$—$CH_2$—$O(CH_2CH_2O)_{2-10}$—$C_8H_{17}$, $(EtO)_2MeSi$—$CH_2$—$O(CH_2CH_2O)_{2-10}$—$C_{12}H_{25}$, $(MeO)_3Si$—$H_2CH_2CH_2NHCH_2CH(OH)CH_2$—$O(CH_2CH_2O)_{2-10}$—$C_8H_{17}$, $(MeO)_3Si$—$CH_2CH_2CH_2NHCH(CH_2OH)CH_2$—$O(CH_2CH_2O)_{2-10}$—$C_8H_{17}$, $(MeO)_3Si$—$H_2CH_2CH_2NHCH_2CH(OH)CH_2$—$O(CH_2CH_2O)_{2-10}$—$C_{12}H_{25}$ and $(MeO)_3Si$—$CH_2CH_2CH_2NHCH(CH_2OH)CH_2$—$O(CH_2CH_2O)_{2-10}$—$C_{12}H_{25}$, where Me is the methyl radical and Et is the ethyl radical.

The compounds of the formula (I) are preferably water-clear to slightly cloudy, colorless to yellowish liquids at room temperature and 1013 hPA. The compounds of the formula (I are standard commercial products and/or can be produced by methods customary in chemistry. For example, the siloxy-substituted polyethers can be produced by addition of epoxy-functional silanes onto standard commercial dewatered alkyl (polyethylene glycol)ether carboxylates, catalyzed with tertiary amines such as 1,4-diazabicyclo[2.2.2]octane.

A further method for producing compounds of the formula (I) consists in the addition of standard commercial dewatered alkyl-polyether glycols onto isocyanato-functional silanes, e.g. 3-isocyanatopropyltrimethoxysilane or (isocyanatomethyl)methyldiethoxysilane, catalyzed with bismuth octanoate or dioctyltin dilaurate.

In a further method, firstly an amine-substituted polyether is produced by addition of propenimine onto standard commercial polyethylene glycols alkyl-terminated at one end. The thus produced polyethylene glycol terminated at one end by 2-amino-propyl ether groups is then reacted with isocyanato-, glycidoxy-, acrylato- or methacrylato-functional silanes, such as 3-isocyanatopropyltrimethoxysilane, (isocyanatomethyl)-methyldiethoxysilane, (3-glycidoxypropyl)trimethoxysilane, (3-glycidoxypropyl)triethoxysilane, (3-acryloxypropyl)trimethoxysilane, (acryloxymethyl)triethoxysilane, 3-(methacryloxypro-pyl)trimethoxysilane or (methacryloxymethyl)triethoxysilane.

In a further method, firstly the silyl-substituted polyether is produced by addition of trialkylsilanes onto standard commercial polyethylene glycols allyl-terminated at one end, catalyzed with tris(triphenylphosphine)rhodium(I) chloride. The thus produced polyethylene glycol terminated at one end by 3-trialkylsilylpropyl groups is then reacted with acryloyl chloride or methacryloyl chloride in the presence of an HCl acceptor in a solvent, such as e.g. triethylamine in diethyl ether. The thus produced polyethylene glycol is terminated at the one end with 3-trialkylsilylpropyl groups and terminated at the other end with an acrylate or methacrylate group and can now be added onto a silane with a primary amino group, such as (3-aminopropyl)trimethoxysilane, (3-amino-propyl)triethoxysilane, N-(2-aminoethyl)(3-aminopropyl)triethoxysilane, N-(2-aminoethyl)(3-aminopropyl)trimethoxysilane, N-(2-aminoethyl)(3-aminopropyl)methyldimethoxysilane.

In a further method, standard commercial polyethylene glycols alkyl-terminated at one end are reacted with acryloyl or methacryloyl chloride in the presence of an HCl acceptor in a solvent, such as e.g. triethylamine in diethyl ether. The thus produced polyethylene glycol is terminated at the one end with alkyl groups and terminated at the other end with an acrylate or methacrylate group and can now be added onto a silane with a primary amino group, such as (3-aminopropyl)trimethoxysilane, (3-aminopropyl)triethoxysilane, N-(2-aminoethyl)(3-aminopropyl)triethoxysilane, N-(2-aminoethyl)(3-amino-propyl)trimethoxysilane, N-(2-aminoethyl)(3-aminopropyl)methyldimethoxysilane.

In a further method, standard commercial polyethylene glycols alkyl-terminated at one end are firstly used to produce the corresponding alcoholates, e.g. by reaction with butyllithium or sodium ethylate. The thus produced alkyl polyethylene glycolate is then reacted with chloroalkylsilanes, such as (3-chloropropyl)trimethoxysilane, (3-chloropropyl)triethoxysilane, (chloromethyl)methyldimethoxysilane or (chloromethyl)triethoxysilane), and purified from the resulting chloride.

In a further method, trialkoxysilanes catalyzed with tris(triphenylphosphine)rhodium(I) chloride are added onto standard commercial polyethylene glycol allyl ethers or vinyl ethers alkyl-terminated at one end.

In a further method, standard commercial polyethylene glycol allyl ethers or vinyl ethers alkyl-terminated at one end are epoxidized, e.g. with peracetic acid. The thus produced polyethylene glycol is terminated at the one end with alkyl groups and carries at the other end an epoxy group and can now be added onto a silane with a primary or secondary amino group, such as (3-aminopropyl)trimethoxysilane, (3-aminopropyl)triethoxysilane, N-(2-aminoethyl)(3-aminopropyl)triethoxysilane, N-(2-aminoethyl)(3-aminopropyl)trimethoxysilane, N-(2-aminoethyl)(3-aminopropyl)methyldimethoxysilane or (N-(n-butyl)-3-aminopropyl) trimethoxysilane.

The compositions according to the invention can be any desired hitherto known types of compositions crosslinkable by condensation reaction which are storage-stable in the absence of water and are crosslinkable to elastomers or resins (so-called RTV compositions). The crosslinkable compositions can be free from fillers, but can also contain active or inactive fillers.

The type and amount of the components customarily used in such compositions are already known. In the context of the present invention, the term "condensation reaction" is also intended to include an optionally preceding hydrolysis step.

Preferably, the inventive compositions crosslinkable by condensation reaction are those which can be produced using
(A) organosilicon compounds with at least two condensable groups and
(B) compounds of the formula (I).

In the context of the present invention, the term "condensable radicals" is also intended to be understood as meaning those radicals which include an optionally preceding hydrolysis step.

The condensable groups which the organosilicon compounds involved in the crosslinking reaction have may be any desired groups, preferably hydroxy, oximato or organyloxy groups, more preferably hydroxy and organyloxy groups, and in particular hydroxy groups.

The organosilicon compounds (A) used according to the invention can be all organosilicon compounds with at least two condensable groups which are useful in compositions crosslinkable by condensation reaction. These may either be pure siloxanes, i.e. ≡Si—O—Si≡ structures, or silcarbanes, i.e. ≡Si—R"—Si≡ structures where R" is a divalent, optionally substituted or heteroatom-interrupted hydrocarbon radical or any desired copolymers having organosilicon groups.

Preferably, the organosilicon compounds (A) are those comprising units of the formula

where
$R^3$ can be identical or different and are optionally substituted hydrocarbon radicals which can be interrupted by oxygen atoms,
$R^4$ can be identical or different and are hydrogen or monovalent, optionally substituted hydrocarbon radicals which can be interrupted by oxygen atoms,
b is 0, 1, 2 or 3, preferably 0, 1 or 2, more preferably 0, and
c is 0, 1, 2 or 3, preferably 1 or 2,
with the proviso that the sum of b+c is less than or equal to 3 and at least two condensable radicals ($OR^4$) are present per molecule.

Preferably, radical $R^3$ is a monovalent hydrocarbon radical having 1 to 18 carbon atoms, optionally substituted with halogen atoms, amino groups, ether groups, ester groups, epoxy groups, mercapto groups, cyano groups or (poly)glycol radicals, where the latter are composed of oxyethylene and/or oxypropylene units, more preferably alkyl radicals having 1 to 12 carbon atoms, in particular the methyl radical. Radical $R^3$, however, can also be a divalent radical which e.g. joins two silyl groups together.

Examples of radicals $R^3$ are the examples given above for radicals R, and also alkoxyalkyl radicals such as the methoxyethyl, the ethoxyethyl or the ethoxyethoxyethyl radicals; gamma-substituted propyl radicals such as the aminopropyl, the N-(2-aminoethyl)-3-aminopropyl, the glycidoxypropyl or the methacryloxypropyl radical; and substituted methyl radicals such as the N-cyclohexylaminome-thyl, the N-phenylaminomethyl, the N,N'-dibutylaminomethyl, the methacryloxymethyl or the N-carbamatomethyl radical.

Examples of divalent radicals $R^3$ are —$CH_2CH_2$—, —$CH_2CH_2CH_2$—, —$CH_2CH_2CH_2CH_2CH_2CH_2CH_2CH_2$—, —$CH_2CH(CH_2CH_2CH_2CH_2CH_2CH_2CH_2CH_3)$—, —$CH_2CH_2$-Ph-$CH_2CH_2$—, —$CH_2CH_2CH_2$—NH—$CH_2CH_2CH_2$— and —$CH_2CH_2CH_2$—NH—$CH_2CH_2$—NH—$CH_2CH_2CH_2$—, where Ph is phenylene radical.

Examples of radicals $R^4$ are the monovalent radicals given for R.

Preferably, radical $R^4$ is hydrogen or an alkyl radical having 1 to 12 carbon atoms, more preferably hydrogen or an alkyl radical having 1 to 6 carbon atoms, in particular hydrogen, methyl, or ethyl.

Most preferably, organosilicon compounds (A) used according to the invention are those of the formula

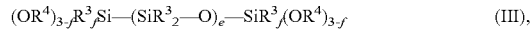

where
$R^3$ and $R^4$ have one of the meanings given above,
e is 30 to 3000 and
f is 1, 2 or 3.

Preferably, f is 2 if $R^4$ is hydrogen, and f is 1 if $R^4$ is other than hydrogen.

Examples of organosilicon compounds (A) are $(MeO)_2MeSiO[SiMe_2O]_{200-2000}SiMe(OMe)_2$, $(HO)Me_2SiO[SiMe_2O]_{200-2000}SiMe_2(OH)$, $(EtO)_2MeSiO[SiMe_2O]_{200-2000}SiMe(OEt)_2$, $(HO)MeViSiO[SiMe_2O]_{200-2000}SiMeVi(OH)$, $(MeO)_2ViSiO[SiMe_2O]_{200-2000}SiVi(OMe)_2$ and $(EtO)_2ViSiO[SiMe_2O]_{200-2000}SiVi(OEt)_2$,
where Me is the methyl radical, Et is the ethyl radical and Vi is the vinyl radical.

The organosilicon compounds (A) preferably have a viscosity of 100 to $10^6$ mPas, more preferably from $10^3$ to 350,000 mPas, in each case at 25° C. The organosilicon compounds (A) are standard commercial products and/or can be produced by methods customary in silicon chemistry.

The compositions preferably comprise component (B) in amounts of from 0.1 to 50 parts by weight, more preferably 0.2 to 10 parts by weight, and in particular 0.3 to 3 parts by weight, in each case based on 100 parts by weight of component (A).

In addition to the above-described components (A) and (B), the compositions according to the invention can now comprise all further substances which are useful in compositions crosslinkable by condensation reaction, such as crosslinkers (C), curing accelerators (D), plasticizers (E), fillers (F), adhesion promoters (G) and additives (H), which are in each case different from components (A) and (B).

The optionally used crosslinkers (C) can be any desired crosslinkers with at least three hydrolyzable radicals, such as silanes or siloxanes with at least three organyloxy groups.

The optionally used crosslinkers (C are preferably organosilicon compounds of the formula

where
$R^5$ can be identical or different and are monovalent, optionally substituted hydrocarbon radicals which can be interrupted by oxygen atoms,
Z can be identical or different and are hydrolyzable radicals and d is 3 or 4,
as well as partial hydrolyzates thereof.

The partial hydrolyzates here may be partial homohydrolyzates, i.e. partial hydrolyzates of one type of organosilicon compound of the formula (IV), or else partial cohydrolyzates, i.e. partial hydrolyzates of at least two different types of organosilicon compounds of the formula (IV).

Although not stated in formula (IV), the organosilicon compounds can have a small fraction of hydroxyl groups, preferably up to at most 5% of all Si-bonded radicals, as a result of production.

The optionally used crosslinkers (C) are preferably partial hydrolyzates of organosilicon compounds of the formula (IV), i.e. those having up to 10 silicon atoms.

Preferably, radical Z is a radical —$OR^6$, where $R^6$ is an optionally substituted hydrocarbon radical, which can be interrupted by oxygen atoms. Examples of Z are alkoxy radicals such as methoxy, ethoxy, n-propoxy, isopropoxy, n-butoxy, isobutoxy, s-butoxy, tert-butoxy and 2-methoxyethoxy radicals, acyloxy radicals such as the acetoxy radical, amino radicals such as the methylamino, dimethylamino, ethylamino, diethylamino and cyclohexylamino radicals, amido radicals such as the N-methylacetamido and benzamido radicals, aminoxy radicals such as the diethylaminoxy radical, oximo radicals such as methylethylketoximo, acetonoximo and methylisobutylketoximo radicals, and enoxy radicals such as the 2-propenoxy radical.

Examples of radicals $R^6$ are the monovalent radicals given for R. Preferably, radical $R^6$ is an alkyl radical having 1 to 12 carbon atoms, more preferably the methyl or ethyl radical.

Examples of radical $R^5$ are the monovalent examples specified for radical R, where hydrocarbon radicals having 1 to 12 carbon atoms are preferred and the methyl, the ethyl, the phenyl and the vinyl radical are particularly preferred.

Preferably, the crosslinkers (C) optionally used in the compositions according to the invention are tetramethoxysilane, tetraethoxysilane, tetrapropoxysilane, tetrabutoxysilane, methyltrimethoxysilane, methyltriethoxysilane, vinyltrimethoxysilane, vinyltriethoxysilane, phenyltrimethoxysilane, phenyltriethoxysilane, N-(tri-methoxysilylmethyl)-O-methylcarbamate, (N-cyclo-hexylaminomethyl) triethoxysilane, (N-morpholinomethyl)triethoxysilane, 1,2-bis(trimethoxysilyl)ethane, 1,2-bis(triethoxysilyl)ethane, methyltris(methylethylketoximo)-silane, vinyltris(methylethylketoximo)silane, vinyl-tris(acetonoximo)silane, vinylbis(acetonoximo)methoxysilane, tetrakis(methylethylketoximo)silane, methyltriacetoxysilane, ethyltriacetoxysilane, vinyltriacetoxysilane, di(tert-butoxy)diacetoxysilane, N,N', N''-tricyclohexyl-1-methylsilanetriamine, 1-methyl-N,N', N''''-tris(1-methyl-propyl)silanetriamine, as well as partial hydrolyzates of said organosilicon compounds, such as e.g. hexaethoxydisiloxane.

The optionally used crosslinkers (C) are more preferably tetramethoxysilane, tetraethoxysilane, tetrapropoxysilane, methyltrimethoxysilane, methyltriethoxysilane, vinyltrimethoxysilane, vinyltriethoxysilane, phenyltrimethoxysilane, 1,2-bis(trimethoxysilyl)ethane, 1,2-bis(triethoxysilyl)ethane, methyltris(methylethylketoximo)-silane, vinyltris(methylethylketoximo)silane, methyltriacetoxysilane, ethyltriacetoxysilane, vinyltriacetoxysilane, and partial hydrolyzates thereof, in particular methyltrimethoxysilane, vinyltriethoxysilane, methyltris(methylethylketoximo)silane, vinyltris(methyl-ethylketoximo)silane, methyltriacetoxysilane, ethyltriacetoxysilane, vinyltriacetoxysilane, and partial hydrolyzates thereof.

The optionally used crosslinkers (C) are standard commercial products and/or can be produced by methods known in silicon chemistry.

If the compositions comprise crosslinkers (C), the amounts are preferably from 0.01 to 20 parts by weight, more preferably 0.5 to 10 parts by weight, and in particular 2 to 6 parts by weight, in each case based on 100 parts by weight of organosilicon compound (A). The compositions according to the invention preferably comprise crosslinkers (C).

As curing accelerators (D), it is possible to use all curing accelerators which are useful in compositions crosslinkable by condensation reaction. Examples of curing accelerators (D) are titanium compounds and organic tin compounds, such as di-n-butyltin dilaurate and di-n-butyltin diacetate, di-n-butyltin oxide, dimethyltin diacetate, dimethyltin dilaurate, dimethyltin dineodecanoate, dimethyltin oxide, dioctyltin diacetate, dioctyltin dilaurate, dioctyltin oxide, and reaction products of these compounds with alkoxysilanes such as tetraethoxysilane, where di-n-butyltin diacetate, dioctyltin dilaurate and dioctyltin oxide in a mixture of 1 part by weight of methyltriethoxysilane hydrolyzate oligomers with on average 10 Si atoms per molecule and 1 part by weight of 3-aminopropyltriethoxysilane are preferred, and dioctyltin oxide in a mixture of 1 part by weight of methyltriethoxysilane hydrolyzate oligomers with on average 10 Si atoms per molecule and 1 part by weight of 3-aminopropyltriethoxysilane is particularly preferred.

If the compositions comprise curing accelerators (D), the amounts are preferably from 0.01 to 3 parts by weight, preferably 0.05 to 2 parts by weight, in each case based on 100 parts by weight of constituent (A). The compositions according to the invention preferably comprise curing accelerators (D).

Examples of plasticizers (E) are dimethylpolysiloxanes end-blocked by trimethylsiloxy groups that are liquid at room temperature, especially with viscosities at 25° C. in the range between 10 and 1000 mPas, organopolysiloxanes that are liquid at room temperature and ambient pressure which consist essentially of —$SiO_{3/2}$— and ≡$SiO_{1/2}$ units, so-called T and M units, as well as high-boiling hydrocarbons, such as e.g. paraffin oils or mineral oils consisting essentially of naphthenic and paraffinic units.

Preferably, plasticizers (E) are dimethylpolysiloxanes end-blocked by trimethylsiloxy groups, with viscosities at 25° C. in the range between 100 and 1000 mPas, and high-boiling hydrocarbons.

If the compositions comprise plasticizers (E), the amounts are preferably from 1 to 300 parts by weight, more preferably 5 to 200 parts by weight, and in particular 10 to 100 parts by weight, in each case based on 100 parts by weight of organosilicon compound (A). The compositions according to the invention preferably comprise plasticizers (E).

Examples of fillers (F) are non-reinforcing fillers, i.e. fillers with a BET surface areas of up to 50 $m^2/g$, such as quartz, diatomatious earth, calcium silicate, zirconium silicate, zeolites, metal oxide powders such as oxides of aluminum, titanium, iron or zinc, or mixed oxides thereof, barium sulfate, calcium carbonate, gypsum, silicon nitride, silicon carbide, boron nitride, glass or plastic powders such as polyacrylonitrile powder; reinforcing fillers, i.e. fillers with a BET surface area of more than 50 $m^2/g$, such as pyrogenically produced silica, precipitated silica, precipitated chalk, carbon black such as furnace and acetylene, black and silicon-aluminum mixed oxides of large BET surface area; fibrous fillers such as asbestos, and also plastic fibers. The fillers can be hydrophobized, for example by treatment with organosilanes or -siloxanes or with stearic acid or by etherification of hydroxyl groups to alkoxy groups. If fillers (F) are used, these are preferably hydrophilic pyrogenic silica and precipitated or ground calcium carbonate.

If the compositions comprise fillers (F), the amounts are preferably from 1 to 300 parts by weight, more preferably 5 to 200 parts by weight, and in particular 10 to 200 parts by weight, in each case based on 100 parts by weight of organosilicon compound (A). The compositions according to the invention preferably comprise fillers (F).

Examples of the adhesion promoters (G) used in the compositions according to the invention are silanes and organopolysiloxanes with functional groups such as those with gycidoxypropyl, aminopropyl or methacryloxypropyl radicals. If, however, another component, such as for example organosilicon compounds (A), (B) or (C) has the mentioned functional groups, it is possible to dispense with addition of adhesion promoters.

If the compositions according to the invention comprise adhesive promoters (G), the amounts are preferably from preferably 0.1 to 50 parts by weight, more preferably 0.5 to 20 parts by weight, and in particular 1 to 10 parts by weight, in each case based on 100 parts by weight of organosilicon compound (A).

Examples of additives (H) are pigments, dyes, fragrances, oxidation inhibitors, agents for influencing electrical properties such as conductive carbon black, flame-retarding agents, photostabilizers, fungicides, agents for prolonging skin formation time such as silanes with an SiC-bonded mercaptoalkyl radical, cell-generating agents, e.g. azodicarbonamide, heat stabilizers, scavengers such as Si—N containing silazanes or silylamides, cocatalysts such as Lewis and Brinsted acids, e.g. sulfonic acids, phosphoric acids, phosphoric acid esters, phosphonic acids and phosphonic acid esters, thixotropic agents such as phosphoric acid esters or polyethylene glycol OH-end-terminated on one or both ends, organic solvents such as alkylaromatics, and also any desired siloxanes which are different from components (A), (B) and (C).

If the compositions according to the invention comprise additives (H), the amounts are preferably from 0.01 to 100 parts by weight, more preferably 0.1 to 30 parts by weight, and in particular 0.3 to 10 parts by weight, in each case based on 100 parts by weight of organosilicon compound (A). The compositions according to the invention preferably comprise additives (H).

Preferably, the compositions according to the invention are those which comprise
(A) organosilicon compounds containing units of the formula (II),
(B) compounds of the formula (I),
(C) crosslinkers of the formula (IV),
optionally,
(D) curing accelerators,
optionally,
(E) plasticizer,
optionally,
(F) fillers,
optionally,
(G) adhesion promoters, and
optionally,
(H) additives.

In particular, the compositions according to the invention are those which comprise
(A) organosilicon compounds containing units of the formula (II),
(B) compounds of the formula (I),
(C) crosslinkers of the formula (IV),
(D) curing accelerators,
optionally,
(E) plasticizers,
optionally,
(F) fillers,
optionally
(G) adhesion promoters and
optionally
(H) additives.

Most preferably, the compositions according to the invention are those which comprise
(A) organosilicon compounds containing units of the formula (III),
(B) compounds of the formula (I),
(C) crosslinkers of the formula (IV),
(D) curing accelerators,
(E) plasticizers,
(F) fillers,
(H) additives, and
optionally,
(G) adhesion promoters.

The compositions according to the invention preferably comprise no further constituents over and above components (A) to (H).

To provide the compositions according to the invention, all constituents can be mixed together in any desired order. This mixing can take place at room temperature and the pressure of the ambient atmosphere, i.e. about 900 to 1100 hPa. If desired, however, this mixing can also take place at higher temperatures, e.g. at temperatures in the range from 35 to 135° C. Furthermore, it is possible to mix occasionally or continuously under reduced pressure such as e.g. at 30 to 500 hPa absolute pressure, in order to remove volatile compounds or air.

The invention further provides a method for producing the compositions according to the invention by mixing the individual constituents.

The individual constituents of the compositions according to the invention can in each case be one type of such a constituent, or else a mixture of at least two different types of such constituents.

For the crosslinking of the compositions according to the invention, the customary water content of air suffices. The crosslinking of the compositions according to the invention preferably takes place at room temperature. If desired, it can also be carried out at higher or lower temperatures than room temperature, e.g. at −5° to 15° C. or at 30° C. to 50° C. and/or by means of concentrations of water exceeding the normal water content of air.

Preferably, the crosslinking is carried out at a pressure from 100 to 1100 hPa, in particular at the pressure of the ambient atmosphere, i.e. about 900 to 1100 hPa.

The present invention further provides moldings produced by crosslinking the compositions according to the invention.

The compositions according to the invention can be used for all purposes for which compositions that are storable with exclusion of water and crosslink upon ingress of water at room temperature to resins or elastomers can be used. The compositions are thus exceptionally suited as sealing compositions for gaps, including vertical gaps, and similar empty spaces of e.g. 10 to 40 mm internal width, e.g. of buildings, land vehicles, water-borne vehicles and aircraft, or as adhesives or putty compositions e.g. in window construction or in the production of glass cabinets, and also e.g. for producing protective coverings including those surfaces subjected to the constant action of freshwater or seawater, or coverings that prevent slipping, or of rubber-elastic moldings, for the coating of surfaces such as structure materials e.g. wood, concrete, metals or plastics, as well for the insulation of electric or electronic devices.

The compositions according to the invention have the advantage that they are easy to produce and even small amounts of compounds of the formula (I) have a very strongly hydrophilizing effect. Moreover, the effect is retained even over a prolonged period, i.e. it is not reduced as a result of the fact that the hydrophilizing layer becomes hydrophobic again as a result of migrating siloxanes.

Furthermore, the compositions according to the invention have the advantage that the surface of the generated moldings exhibit permanent hydrophilicity and at the same time have excellent adhesion to building materials, such as wood, concrete and metals or plastics.

The crosslinkable compositions according to the invention have the advantage that they are characterized by very high storability and a high crosslinking rate.

In the examples described below, all viscosity data relate to a temperature of 25° C. Unless stated otherwise, the examples below are carried out at a pressure of the ambient atmosphere, i.e. at about 1000 hPa, and at room temperature, i.e. at about 23° C., or at a temperature which is established upon combining the reactants at room temperature without additional heat or cooling, and also at a relative atmospheric humidity of about 50%. Furthermore, all data for parts and percentages refer to the weight, unless stated otherwise.

In order to assess the contact angle of the vulcanizate surface (test 1), the crosslinkable compositions are applied to PE film in a 2 mm-thick layer in each case and, after storage for 7 days at 23° C. and 50% relative atmospheric humidity, the left and right contact angles are determined at three measurement points using water drops of about 13 μl in volume after 5 min. The average contact angle from all three measurements is given in degrees, rounded to the next integer.

In order to assess the run-off angle of water drops on the surface (test 2), the crosslinkable compositions are applied to PE film in a 2 mm-thick layer in each case and cured for 7 days at 23° C. and 50% relative atmospheric humidity. The sheet is then placed in a quadrant such that the area from horizontal (=0°) to perpendicular (=90°) is covered with the sheet. At an angle greater than 50°, four water drops of 6 μl, 10 μl, 15 μl and 20 μl are applied and the run-off angle is read off after 5 min, if the drops are no longer moving, at the front edge of the drop. The values are ascertained with an accuracy of +/−1 degree and noted.

Production of Product 1

In a glass flask with Liebig condenser and receiver, 100 g of glycolic ethoxylate lauryl ether (Mn=460 g/mol) (commercially available under the name AKYPO RLM 45 CA from KAO Chemicals GmbH, D-Emmerich) were stirred at 100° C. and 20 mbar until no more water separates off. After aeration with nitrogen, 47 g of (3-glycidoxypropyl)trimethoxysilane (commercially available under the trade name GENIOSIL® GF 80 from Wacker Chemie AG, D-Munich) and 0.5 g of 1,4-diazabicyclo[2.2.2]octane (commercially available as DABCO® from Sigma-Aldrich Chemie GmbH, D-Taufkirchen) were added and the mixture was stirred for 2 hours at 100° C. Cooling and filtration gives a yellowish liquid. $^{13}$C-NMR and titration were used to establish a degree of addition of more than 80%.

135 g of product were obtained, which consists primarily of the following substances: $(MeO)_3Si$—$CH_2CH_2CH_2OCH_2CH(OH)CH_2OC(=O)CH_2$—$O$—$(CH_2CH_2O)_{2-6}$—$(CH_2)_{11-13}CH_3$ and $(MeO)_3Si$—$CH_2CH_2CH_2OCH_2CH(CH_2(OH))OC(=O)CH_2$—$O$—$(CH_2CH_2O)_{2-6}$—$(CH_2)_{11-13}CH_3$.

Production of Product 2

In a glass flask with Liebig condenser and receiver, 103 g of isotridecanol, ethoxylated (commercially available under the name Marlipal O 13/60 from Sasol Germany GmbH, D-Hamburg) were stirred at 80° C. and 6 mbar until no more water separates off. After aeration with nitrogen, 47.1 g of (3-isocya-natopropyl)trimethoxysilane (commercially available under the trade name GENIOSIL® GF 40 from Wacker Chemie AG, D-Munich) were added and the mixture was stirred for 30 minutes. Then, 0.015 g of bismuth 2-ethylhexanoate (commercially available from Gelest Inc., D-Frankfurt am Main) was added and the mixture was stirred for 2 hours at 80° C. After cooling to 60° C., 0.76 g of methanol was added and the mixture was stirred for 30 minutes and the product was drawn-off under argon in a moisture-sealed manner.

Before the methanol addition, the NCO content was 0.005%, determined with IR.

150 g of product are obtained that consist essentially of iso-$C_{13}H_{27}$—$O(CH_2CH_2O)_{4-8}$—$C(=O)$—$NH$—$CH_2$—$CH_2$—$CH_2$—$Si(OMe)_3$.

Production of Product 3

Dry air were passed through a mixture of 9.38 g (24 mmol) of α-allyl-ω-hydroxypoly(ethylene glycol) with a molecular weight of ca. 390 g/mol, 2.98 g (25 mmol) of triethylsilane and 0.0448 g of Wilkinson catalyst (tris(triphenylphosphine)rhodium(I) chloride) at room temperature for 1 hour. The mixture was then further stirred at room temperature for a period of 16 hours. Then, a solution consisting of 1.0 g of acetic acid, 1 ml of distilled water and 50 ml of THF was added and the mixture was stirred for a further 5 hours at room temperature. Finally, 5 g of MgO were added, then the solid was filtered off and the THF was drawn off under reduced pressure. The residue is dissolved in acetonitrile. This solution was extracted with hexane (3×10 ml) and then the acetonitrile was distilled off under reduced pressure. The residue was further purified by feeding it through a short column filled with silica gel, using a mixture of methylene chloride/hexane (1:1) as eluent. After evaporating off the solvent, 9.1 g (74%) of pure α-hydroxy-ω-triethylsilylpropylpolyethylene glycol were obtained.

8.0 g (15.9 mmol) of the thus obtained α-hydroxy-ω-triethylsilylpropylpolyethylene glycol and 16.2 g (159 mmol) of triethylamine were dissolved in 200 ml of diethyl ether. Over the course of 30 min, 1.6 ml (17.5 mmol) of acryloyl chloride were added dropwise to this solution at 0° C. with stirring. When the addition was complete, the cooling was removed and the mixture was further stirred for a period of 16 hours at room temperature. The precipitated solid was then separated off and the ethereal solution was freed from the solvent under reduced pressure. The residue was in turn purified over a silica gel column using methylene chloride/hexane as eluent. This gave 7.63 g (81%) of the desired target product α-acryloyl-ω-triethylsilylpropylpoly(ethylene glycol) (APC2). The total yield of both steps was 60%.

A larger amount of APC2 (M=550 g/mol) was produced in accordance with the procedure described above and 100 g (0.18 mol) of it were thoroughly mixed in a glass bottle with 32 g of (3-aminopropyl)trimethoxysilane. After storage for 7 days at room temperature, a double bond could no longer be detected in the $^{13}$C-NMR.

132 g of a mixture consisting of $(CH_3CH_2)_3SiCH_2CH_2CH_2O(CH_2CH_2O)_{6-9}$—$C(=O)CH_2CH_2$ $NHCH_2CH_2CH_2Si(OMe)_3$ and $(CH_3CH_2)_3$ $SiCH_2CH_2$ $CH_2O(CH_2CH_2O)_{6-9}$—$C(=O)CH(CH_3)NHCH_2CH_2CH_2Si(OMe)_3$ are obtained.

Production of Product 4

The process for the production of product 3 was repeated using firstly 9.98 g (28.5 mmol) of α-allyl-ω-hydroxypoly(ethylene glycol) with a molecular weight of ca. 390 g/mol and 9.12 g (31.4 mmol) of tri-n-hexylsilane. 9.8 g (53.5%) of pure α-hydroxy-ω-tri-n-hexylsilylpropylpolyethylene glycol were obtained, of which 8.0 g (11.8 mmol) were reacted in accordance with the procedure described for the production of product 3 with acryloyl chloride to give 6.9 g (78%) of target product α-acryloyl-ω-tri-n-hexylsilylpropylpoly(ethylene glycol) (APC6).

The total yield of both steps was 41.7%.

A larger amount of APC6 (M=674 g/mol) was produced in accordance with the procedure described above and 100 g (0.15 mol) of it were thoroughly mixed in a glass bottle with 33 g (0.15 mol) of N-(2-aminoethyl(3-aminopropyl))trimethoxysilane. After storage for 7 days at room temperature, a double bond could no longer be detected in the $^{13}$C-NMR.

133 g of a mixture consisting of $(n-C_6H_{13})_3SiCH_2CH_2CH_2O(CH_2CH_2O)_{6-9}$—C(=O)$CH_2CH_2NHCH_2CH_2NH$—$CH_2CH_2CH_2Si$ $(OMe)_3$ and $(n-C_6H_{13})_3SiCH_2CH_2CH_2O(CH_2CH_2O)_{6-9}$—C(=O)CH$(CH_3)NHCH_2CH_2NHCH_2CH_2CH_2Si(OMe)_3$ are obtained.

Production of Product A5

In a glass flask with Liebig condenser and receiver, 105 g of glycolic acid ethoxylate capryl ether (Mn=547 g/mol) (commercially available under the name AKYPO LF 2 from KAO Chemicals GmbH, D-Emmerich) were stirred at 100° C. and 20 mbar until no more water separates off. After aeration with nitrogen, 45 g of (3-glycidoxypropyl)trimethoxysilane (commercially available under the trade name GENIOSIL® GF 80 from Wacker Chemie AG, D-Munich) and 0.5 g of DABCO® (commercially available as 1,4-diazabicyclo[2.2.2]octane from Sigma-Aldrich Chemie GmbH, D-Taufkirchen) were added and the mixture was stirred for 2 hours at 100° C. Cooling and filtration gives a pale yellow liquid. $^{13}$C-NMR and titration were used to establish a degree of addition of ca. 85%.

140 g of product are obtained which consist primarily of the following substances: $(CH_3O)_3Si$—$CH_2CH_2CH_2OCH_2CH(OH)CH_2OC$(=O)$CH_2$—O$(CH_2CH_2O)_{6-10}$—$(CH_2)_7CH_3$ and $(CH_3O)_3Si$—$CH_2CH_2CH_2OCH_2CH$$(CH_2(OH))OC$(=O)$CH_2$—O$(CH_2CH_2O)_{6-10}$—$(CH_2)_7$$CH_3$.

EXAMPLE 1

1400 g of an α,ω-dihydroxypolydimethylsiloxane with a viscosity of 80 000 mPa·s, 454 g of a trimethylsilyl-end-blocked polydimethylsiloxane (PDMS) with a viscosity of 1000 mPa·s and 243 g of a hydrocarbon mixture with a kinematic viscosity (at 40° C.) of 5.9 mm$^2$/s, a viscosity-density constant of 0.79 and a boiling range from 305 to 340° C. were mixed in a planetary mixer with 66 g of ethyltriacetoxysilane, 25 g of methyltriacetoxysilane and 3 g of diacetoxydi-tert-butoxysilane for 5 minutes. Then, 220 g of pyrogenic silica with a specific surface area of 150 m$^2$/g (commercially available under the trade name HDK® V15D from Wacker Chemie AG, D-Munich) were worked in. After homogenization for 20 minutes at 100 hPa, 2.4 g of polyalkylene glycol, consisting of ca. 13 ethylene oxide units and 1 propylene oxide unit, with an average molar mass of 600 g/mol (commercially available under the name PR 600 from Clariant GmbH, D-Frankfurt am Main), 24 g of product 1 and 0.24 g of dibutyltin diacetate were mixed in at 100 hPa. The product produced was drawn off for the purposes of storage into moisture-tight packaging.

Test 1 and test 2 were carried out with the composition thus obtained. The results can be found in table 1.

EXAMPLE 2

The procedure described in example 1 is repeated except that 24 g of product 2 are used instead of product 1.
The results can be found in table 1.

EXAMPLE 3

The procedure described in example 1 is repeated except that 24 g of product 3 are used instead of product 1.
The results can be found in table 1.

EXAMPLE 4

The procedure described in example 1 is repeated except that 24 g of product 4 are used instead of product 1.
The results can be found in table 1.

EXAMPLE 5

The procedure described in example 1 is repeated except that 24 g of product 5 is used instead of product 1.
The results can be found in table 1.

Comparative Example 1 (C1)

The procedure described in example 1 is repeated except that no product A1 is used. The results can be found in table 1.

Comparative Example 2 (C2)

The procedure described in example 1 is repeated except that 24 g of N-(triethoxysilylpropyl)-O-polyethylene oxide urethane with a molar mass of 400-500 (commercially available from ABCR GmbH & Co. KG, D-Karlsruhe) are used instead of product 1.
The results can be found in table 1.

Comparative Example 3 (C3)

The procedure described in example 1 is repeated except that 24 g of polyalkylene glycol, consisting of ca. 13 ethylene oxide units and 1 propylene oxide unit, with an average molar mass of 600 g/mol (commercially available under the name PR 600 from Clariant GmbH, D-Frankfurt am Main) are used instead of product 1.
The results can be found in table 1.

TABLE 1

| Example | Contact angle, in degrees | Roll-off angle 20 μl, in degrees | Roll-off angle 15 μl, in degrees | Roll-off angle 10 μl, in degrees | Roll-off angle 6 μl, in degrees |
|---|---|---|---|---|---|
| 1 | 61 | 5 | 5 | 10 | 20 |
| 2 | 87 | 10 | 15 | 20 | 35 |
| 3 | 66 | 7 | 12 | 20 | 33 |
| 4 | 69 | 10 | 18 | 25 | 38 |
| 5 | 58 | 5 | 8 | 12 | 20 |
| C1 | 104 | >50 | >50 | >50 | >50 |
| C2 | 101 | 26 | 32 | >50 | >50 |
| C3 | 100 | 25 | 38 | >50 | >50 |

The invention claimed is:

1. A single-component organosilicon composition, storable with the exclusion of water and crosslinkable to an elastomer upon ingress of water at room temperature, comprising compound(s) of the formula $$(R^1O)_aR_{3-a}Si\text{-}A\text{-}O(CH_2CH_2\text{---}O)_x\text{---}R^2 \qquad (I),$$

where
R each are identical or different monovalent, optionally substituted hydrocarbon radicals,
$R^1$ each are identical or different and are hydrogen or a monovalent, optionally substituted hydrocarbon radical,
A is a divalent, optionally substituted hydrocarbon radical bonded via carbon onto Si and O, which optionally contains hydroxyl, ester (—O—C(=O)—), amide (—N—C(=O)—), urethane (—O—C(=O)—NH—), urea (—N—C(=O)—NH—), thioester (—S—C (=O)—), thioether (—S—), ether (—O—), imine (—N—) and/or carbonyl groups (—C(=O)—),
$R^2$ each independently is a monovalent, linear or branched hydrocarbon radical having 8 to 22 carbon atoms, where a carbon atom can be replaced by a silicon atom bonded via carbon onto O,
a is 1, 2 or 3 and
x is an integer from 1 to 20,
and further comprising:
at least one organosilicon compound with at least two condensable groups.

2. The crosslinkable composition of claim 1, wherein at least one radical A is —CH$_2$CH$_2$CH$_2$OCH$_2$CH(OH)CH$_2$OC (=O)CH$_2$—, —CH$_2$CH$_2$CH$_2$OCH$_2$CH(CH$_2$(OH))OC (=O)CH$_2$—, —C(=O)—NH—CH$_2$—CH$_2$—CH$_2$—, —C(=O)—NH—CH$_2$—, —CH$_2$CH$_2$CH$_2$NHC(=O) CH$_2$—, —CH$_2$CH$_2$CH$_2$NHCH$_2$CH$_2$NHC(=O)CH$_2$—, —CH$_2$CH$_2$CH$_2$NHC(=O)NH-CH(CH$_3$)CH$_2$—, —C(=O) CH(CH$_3$)CH$_2$NHCH$_2$CH$_2$CH$_2$—, —C(=O)CH$_2$CH$_2$— NHCH$_2$CH$_2$CH$_2$—, —C(=O)C(CH$_3$)$_2$NHCH$_2$CH$_2$CH$_2$—, —C(=O)CH(CH$_3$)—NHCH$_2$CH$_2$CH$_2$—, —C(=O)CH (CH$_3$)CH$_2$NHCH$_2$CH$_2$NHCH$_2$CH$_2$CH$_2$—, —C(=O)C (CH$_3$)$_2$NHCH$_2$CH$_2$NHCH$_2$CH$_2$CH$_2$—, —CH$_2$CH$_2$CH$_2$—, —CH$_2$—, —C(=O) CH$_2$CH$_2$NHCH$_2$CH$_2$NHCH$_2$CH$_2$CH$_2$—, —C(=O)CH (CH$_3$)NHCH$_2$CH$_2$NHCH$_2$CH$_2$CH$_2$—, —CH$_2$CH$_2$CH$_2$NHCH$_2$CH(OH)CH$_2$—, —CH$_2$CH$_2$CH$_2$NHCH$_2$CH$_2$NHCH$_2$CH(OH)CH$_2$—, —CH$_2$CH$_2$CH$_2$NHCH(CH$_2$OH)CH$_2$— or —CH$_2$CH$_2$CH$_2$NHCH$_2$CH$_2$NHCH(CH$_2$OH)CH$_2$.

3. The crosslinkable composition of claim 1, wherein x is an integer from 2 to 10.

4. The crosslinkable composition of claim 2, wherein x is an integer from 2 to 10.

5. The crosslinkable composition of claim 1, which comprises compound(s) of the formula (I) in amounts of from 0.1 to 50 parts by weight, based on 100 parts by weight of the at least one organosilicon compound with two condensable groups.

6. A single-component organosilicon composition, storable with the exclusion of water and crosslinkable to an elastomer upon ingress of water at room temperature, comprising compound(s) of the formula $$(R^1O)_aR_{3-a}Si\text{-}A\text{-}O(CH_2CH_2\text{---}O)_x\text{---}R^2 \qquad (I),$$

where
R each are identical or different monovalent, optionally substituted hydrocarbon radicals,
$R^1$ each are identical or different and are hydrogen or a monovalent, optionally substituted hydrocarbon radical,
A is a divalent, optionally substituted hydrocarbon radical bonded via carbon onto Si and O, which optionally contains hydroxyl, ester (—O—C(=O)—), amide (—N—C(=O)—), urethane (—O—C(=O)—NH—), urea (—N—C(=O)—NH—), thioester (—S—C (=O)—), thioether (—S—), ether (—O—), imine (—NH—) and/or carbonyl groups (—C(=O)—),
$R^2$ each independently is a monovalent, linear or branched hydrocarbon radical having 8 to 22 carbon atoms, where a carbon atom can be replaced by a silicon atom bonded via carbon onto O,
a is 1, 2 or 3 and
x is an integer from 1 to 20,
and further comprising:
(A) at least one organosilicon compound containing units of the formula (II), $$R^3_c(OR^4)_bSiO_{(4-b-c)/2} \qquad (II),$$

where
$R^3$ are each identical or different and are optionally substituted hydrocarbon radicals optionally interrupted by oxygen atoms,
$R^4$ are each identical or different and are hydrogen or a monovalent, optionally substituted hydrocarbon radical optionally interrupted by oxygen atoms,
b is 0, 1, 2 or 3, and
c is 0, 1, 2 or 3,
with the proviso that the sum of b+c is less than or equal to 3 and at least two condensable radicals (OR$^4$) are present per molecule,
(B) at least one crosslinker of the formula (IV), $$Z_dSiR^5_{(4-d)} \qquad (IV),$$

where
$R^5$ are identical or different and are monovalent, optionally substituted hydrocarbon radicals optionally interrupted by oxygen atoms,
Z are identical or different and are hydrolyzable radicals, and d is 3 or 4,
as well as partial hydrolyzates thereof,
(C) optionally, a curing accelerator,
(D) optionally, a plasticizer,
(E) optionally, a filler,
(F) optionally, an adhesion promoter, and
(G) optionally, further additives different from the compound of the formula (I) and difference from (A) through (F).

7. The crosslinkable composition of claim 6, wherein b is 0, 1, or 2.

8. The crosslinkable composition of claim 6, wherein c is 1 or 2.

9. The crosslinkable composition of claim 6, wherein c is 1 or 2.

10. A method for producing a composition of claim 1, comprising mixing the individual constituents together.

11. A molding produced by crosslinking a composition of claim 1.

12. The crosslinkable composition of claim 6, wherein at least one radical A is —CH$_2$CH$_2$CH$_2$OCH$_2$CH(OH)CH$_2$OC (=O)CH$_2$—, —CH$_2$CH$_2$CH$_2$OCH$_2$CH(CH$_2$(OH))OC (=O)CH$_2$—, —C(=O)—NH—CH$_2$—CH$_2$—CH$_2$—, —C(=O)—NH—CH$_2$—, —CH$_2$CH$_2$CH$_2$NHC(=O) CH$_2$—, —CH$_2$CH$_2$CH$_2$NHCH$_2$CH$_2$NHC(=O)CH$_2$—, —CH$_2$CH$_2$CH$_2$NHC(=O)NH-CH(CH$_3$)CH$_2$—, —C(=O) CH(CH$_3$)CH$_2$NHCH$_2$CH$_2$CH$_2$—, —C(=O)CH$_2$CH$_2$— NHCH$_2$CH$_2$CH$_2$—, —C(=O)C(CH$_3$)$_2$NHCH$_2$CH$_2$CH$_2$—, —C(=O)CH(CH$_3$)—NHCH$_2$CH$_2$CH$_2$—, —C(=O)CH (CH₃)CH₂NHCH₂CH₂NHCH₂CH₂CH₂—, —C(═O)C(CH₃)₂NHCH₂CH₂NHCH₂CH₂CH₂—, —CH₂CH₂CH₂—, —CH₂—, —C(═O)CH₂CH₂NHCH₂CH₂NHCH₂CH₂CH₂—, —C(═O)CH(CH₃)NHCH₂CH₂NHCH₂CH₂CH₂—, —CH₂CH₂CH₂NHCH₂CH(OH)CH₂—, —CH₂CH₂CH₂NHCH₂CH₂NHCH₂CH(OH)CH₂—, —CH₂CH₂CH₂NHCH(CH₂OH)CH₂—or —CH₂CH₂CH₂NHCH₂CH₂NHCH(CH₂OH)CH₂.

\* \* \* \* \*